June 17, 1941. A. C. HOFFMAN Re. 21,831

NASAL INHALER

Original Filed Aug. 6, 1937

INVENTOR
Allan C. Hoffman
BY
H. F. Johnston
ATTORNEY

Reissued June 17, 1941 Re. 21,831

UNITED STATES PATENT OFFICE 21,831

NASAL INHALER

Allan C. Hoffman, Milldale, Conn., assignor to Scovill Manufacturing Company, Waterbury, Conn., a corporation of Connecticut Original No. 2,191,015, dated February 20, 1940, Serial No. 157,710, August 6, 1937. Application for reissue October 30, 1940, Serial No. 363,580

1 Claim. (Cl. 128—198)

This invention relates to new and useful improvements in inhalers and particularly of the type using a medicated filler or a crystallized or granular substance adapted to produce vapors or fumes for inhalation in the treatment of nose and throat ailments.

One of the objects of this invention is to construct an inhaler container of relatively few parts made preferably of drawn metal shells and having a means for effectively sealing the device so that it will not lose any of its strength from the time that it is charged with an inhalant until the device is merchandised from the retail store.

A further object is to produce an inhalant container of neat appearance, simple and inexpensive construction, easily operated, and designed to be carried in the vest pocket or in the handbag convenient for immediate use.

A still further object of the invention is to provide a medicament inhaler container for holding a medicament of a volatile nature with both inlet and discharge apertures in which such container is associated with a cover for enveloping both the inlet and discharge apertures and in which there is associated with said container and cover a single sealing means so situated relatively to said container and cover as to be engageable with a part carried for the purpose on the cover in a position to sealingly impress itself mutually with said sealing device to cause sealing of both the inlet and discharge apertures, and wherein there is provided between the container and cover mutually acting connecting means which will not only serve to unite the cover to the container against accidental or casual displacement but also functions to move the container and cover relatively to one another in a direction to cause said part of the cover to impress itself in said sealing means.

A still further object of the invention is to provide a nasal inhaler of the character indicated in the foregoing paragraph in which an enlarged head or flange on the container extends outwardly a substantial distance from the normal diameter of the body of such container and is of a width to permit a convenient grip on the same to handle and support the container both when the cover member is thereon and when the cover member is removed and the container held in the act of use; and the invention further contemplates the use of such enlarged head or flange on the container body as a repository for a sealing gasket cooperating with an enlargement or bead portion at the open end of the cover member to effect a hermetic seal for the device, in which the screw threads cooperate to move such enlargement and gasket tightly together to prevent loss of the inhalant material through evaporation and the device from becoming offensively odorous in the pocket of the user.

The invention will be better understood from the detailed description which follows when considered in conjunction with the accompanying drawing, showing certain preferred embodiments of the invention, wherein.

Figure 3:
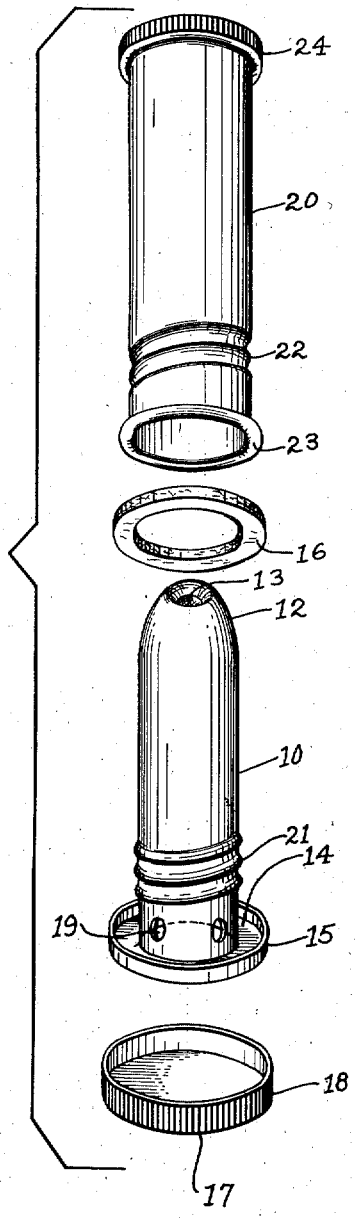
Figure 3 shows an exploded view of the several parts of the inhaler as they appear before assembly.
Figure 1:
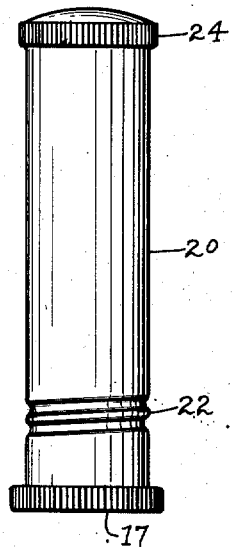
Figure 1 represents a side elevation of the inhaler.
Figure 2:
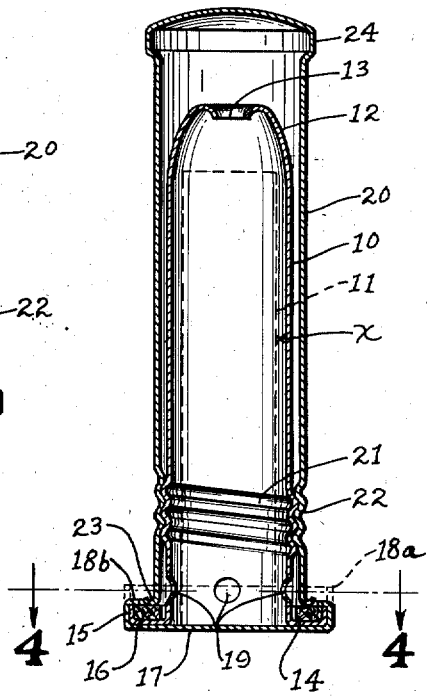
Figure 2 is a longitudinal vertical section through the same on a slightly enlarged scale.
Figure 4:
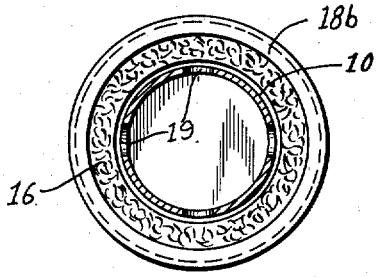
Figure 4 is a transverse section through the device, taken along the line 4—4 of Figure 2 with the cap removed.

Referring now to the drawing, wherein like numerals designate like parts throughout the several views; the numeral 10 indicates a relatively long hollow container shell within which may be disposed a suitable filler 11 preferably made of a rolled cotton wad or other substance of like physical absorbent characteristics (shown by dotted outline in Figure 2), adapted to be saturated with a medicament of a volatile nature. The diameter of the filler 11 is shown as being somewhat less than the interior diameter of the container shell, thus providing a surrounding air passage designated by the letter X (Fig. 2) to allow for a relatively free and unobstructed air passage therethrough.

The upper end of the shell 10 is formed with a smooth conoidal shape adaptable for insertion into a person's nostril. The apex of the conoidal end 12 is formed or spun inwardly and surrounds a single discharge aperture 13, a construction presenting no sharp edges capable of inflicting injury upon the user.

The lower end of the container shell 10 is formed outwardly with an integral supporting flange 14 terminating in an upstanding circumferential wall 15, thus providing an annular channel capacitated for receiving a suitable sealing washer or gasket 16. After the filler 11 is treated with the desired medicament, or in fact any inhalant substance may be loaded into the container shell 10, a sealing cap 17 is affixed to the lower end of said container shell 10 holding the filler 11 permanently there within. The sealing cap 17 is designed to initially telescope over the upstanding wall 15 of the flange 14 and is then permanently secured thereto by spinning over or otherwise forming inwardly the upper end 18a of the peripheral wall 18 of said cap, as shown by dotted outline in Figure 2, to provide a retention flange 18b overlying the upper edge of the flange wall 15. This retention flange 18b is extended inwardly sufficiently to embrace the outer portion of the upper surface of the washer 16 for holding it in position and leaving the greater area of the upper surface of the washer exposed for reasons to be described later.

Air is adapted to be drawn into the interior of the sealed container shell 10 by means of one or more apertures 19 cut out of the wall thereof adjacent the lower end of said container just above the upper surface of the sealing washer 16.

In order to produce an effective sealing means for the inhaler container 10 when not in use, a long cylindrical hollow cover 20 is designed to telescope over substantially the entire length of said shell 10 and then be detachably secured thereto as by a threading operation. The construction for effecting this telescoping and threading connection between parts 10 and 20 is effected by producing an expanded rolled thread 21 on the shell 10 adjacent its lower portion; and the cap, in turn, is provided with an intermediate inwardly formed rolled thread 22 of corresponding pitch and location.

The lower extremity of the cover member 20 is provided with an outwardly formed partially rolled bead 23. When the cover 20 has completed its threaded operation with the shell 10, the complementary bead 23 is adapted by nature of its shape to impress itself into the sealing washer 16 without danger of cutting or mutilating the same, and thus assure a hermetical seal between the parts 10 and 20.

In order to facilitate the manipulation of the cover member 20, the upper end of said cover 20 is formed with a relatively narrow expanded section 24 having an exterior knurl for gripping purposes. The outer surface of the peripheral wall 15 of the sealing cap 16 is likewise provided with a knurl to assist in the handling of the article.

As pointed out in the objects of this specification, it is within the purview of this invention, if desired, to employ crystal or granular volatile substances in this inhaler, in which case the outlet opening 13 in the end of the container shell 10 will be closed and provided with a number of smaller openings, and also the intake openings at the opposite end will necessarily be made smaller and of a size to preclude the escape of the crystal or granular substances therethrough.

In practice, after the container shell 10 has been charged or filled with the desired inhalant, it is used by applying the conoidal end 12 to the nostrils and inhaling. This causes a flow of air to enter the inlet ports 19, pass through the annular space X surrounding the filler 11 or through the interstices of granular and crystal substances when the latter is used, and become saturated or charged with the fumes or vapors in its passage to the outlet port 13. After the inhaler has been used, the cap 20 is slipped or telescoped over the shell 10 until the adjacent convolutions of the threads 20 and 22 of shell 10 and cover 20 respectively contact each other after which one or two turns of the cover 20 will interlock and hermetically seal the parts.

It will be noted that the part 23 mating with the gasket 16 is at the open end portion of the cover 20 to the end that a single sealing means formed cooperatively by said part or bead 23 and the gasket 16 may suffice to seal the entire space between the cover and container, sealing both the inlet apertures 19 and discharge aperture 13 and also sealing the space in and about the threads 22.

The threads 22 perform the double function of so associating the container and cover 20 that the same may not be relatively displaced in an axial direction accidentally or casually, and in the second place by rotating one member relatively to the other the threads 22 develop a strong wedging action in moving the cover 20 and its part 23 relatively to the container 10 so as to forcibly impress the sealing part 23 against its sealing mate 16.

The part 23 engages the inner circular portion of the gasket 16 within the confines of the upper end 18a of the cap 17. The gasket 16 also cooperates with this overturned end 18a to seal the space between the walls 15 and 18 and the flange 14 and bottom of the cap 17 whereby the volatile contents of the container 10 may not leak away through this outlet.

It will be appreciated that the improved construction affords an enlarged head or base flange upon the lower part of the container which subserves a dual function; first, by its very diametrical enlargement, as well as by its axial depth, to offer facilities in the manipulation of the inhaler, and in the second place providing a suitable seat for a washer or gasket presented outwardly of the container and in a position relatively to the cover member to receive forcibly thereagainst the enlarged flange or other part 23 at the lower end of the cover 20 by which a seal for the entire interior device is secured. The enlarged head or flange is constructed with a channel which is substantially U-shaped in cross section for the better reception and retention of the washer or gasket. This enlarged operating head is located at a convenient position, namely at the lower part of the container and removed from the inhalant opening 13, to create convenience in the manipulation and use of the device and to facilitate handling this enlarged part may be formed with a knurled surface 17.

It will be apparent that while there are employed certain details of construction for the purpose of adequately disclosing the invention, various changes or modifications of the construction herein shown and described, may be made within the scope of the appended claim without departing from the spirit of this invention or sacrificing its advantages.

What is claimed is:

In an inhalant device, a container shell having one end formed with a tapering nozzle portion and the opposite end open for receiving an inhalant material therein, the apex of said nozzle end having a discharge aperture, a flange extending outwardly from the open end of said shell and having an upstanding peripheral wall defining an annular channel, a sealing gasket disposed within said channel, a closure cap covering the open end of said container shell and having a part overlying the upper edge of said peripheral wall and extending inwardly of said peripheral wall to embrace a portion of said gasket to retain the latter in place, said shell having ingress means adjacent said washer, and a cover means having detachable interlocking engagement with the intermediate portion of said shell and engaging said gasket for hermetically sealing said device.

ALLAN C. HOFFMAN.